United States Patent [19]

Sasaki et al.

[11] Patent Number: 5,160,721
[45] Date of Patent: Nov. 3, 1992

[54] PROCESS FOR MAINTAINING HIGH LEVEL OF YIELD OF ACRYLONITRILE AND HYDROGEN CYANIDE IN AMMOXIDATION OF PROPYLENE

[75] Inventors: Yutaka Sasaki; Yutaka Kiyomiya; Toshio Nakamura; Kunio Mori; Akimitsu Morii, all of Kanagawa, Japan

[73] Assignee: Nitto Chemical Industry Co., Ltd., Tokyo, Japan

[21] Appl. No.: 253,526

[22] Filed: Oct. 5, 1988

[30] Foreign Application Priority Data

Oct. 5, 1987 [JP] Japan .................................. 62-249707
Jul. 26, 1988 [JP] Japan .................................. 63-184522

[51] Int. Cl.$^5$ ...................... C01C 3/02; C07C 253/26
[52] U.S. Cl. ...................................... 423/376; 558/322
[58] Field of Search ......................... 423/376; 558/322

[56] References Cited

U.S. PATENT DOCUMENTS 4,124,631  11/1978  Hayami et al. .
4,409,122  10/1983  Kleuskens et al. .
4,536,483   8/1985  Sasaki et al. ........................ 423/376
4,618,593  10/1986  Sasaki et al. .

FOREIGN PATENT DOCUMENTS 0057041  1/1982  European Pat. Off. .
2280428  8/1975  France .
59-139938 11/1984  Japan .
2163365  5/1982  United Kingdom .

OTHER PUBLICATIONS

Patent Abstracts of Japan, vol. 8, No. 260, Nov. 29, 1984, JP 59-139938.
Translation (English) of Claims of JPA No. 59139938.

Primary Examiner—Wayne Langel
Attorney, Agent, or Firm—Sughrue, Mion, Zinn, Macpeak & Seas

[57] ABSTRACT

A process for conducting long-term ammoxidation of propylene in the presence of a metal oxide catalyst for ammoxidation of propylene at a temperature of from 300° C. to 500° C. to produce acrylonitrile and hydrogen cyanide, wherein in the process each of (A) elemental phosphorus or a phosphorus compound and (B) elemental tellurium or a tellurium compound is added as a regenerating agent at least once to the ammoxidation reaction system in accordance with the progress of the reaction, the regenerating agent (A) being added when the yields of both of acrylonitrile and hydrogen cyanide are reduced, and the regenerating agent (B) is chosen when the yield of acrylonitrile is reduced and the yield of hydrogen cyanide is unchanged or increased, to thereby maintain high levels of yields of acrylonitrile and hydrogen cyanide.

9 Claims, No Drawings

PROCESS FOR MAINTAINING HIGH LEVEL OF YIELD OF ACRYLONITRILE AND HYDROGEN CYANIDE IN AMMOXIDATION OF PROPYLENE

FIELD OF THE INVENTION

This invention relates to an improvement in ammoxidation of propylene, and, more particularly, to a process of ammoxidation of propylene to obtain acrylonitrile and hydrogen cyanide in yields maintained at high level.

BACKGROUND OF THE INVENTION

A number of catalysts for ammoxidation of propylene have been proposed. Examples of catalysts known to be useful in ammoxidation of propylene include metal oxide systems, such as molybdenum-bismuth catalysts, iron-antimony catalysts, uranium-antimony catalysts, molybdenum-tellurium catalysts, etc., as described in JP-B-36-5870 (corresponding to U.S. Pat. No. 2,904,580), JP-B-37-14075 (corresponding to U.S. Pat. No. 3,152,170), JP-B-38-19111, JP-B-40-24367 (corresponding to U.S. Pat. No. 3,308,151), JP-B-38-17967 (corresponding to U.S. Pat. No. 3,226,422), JP-B-39-8214 (corresponding to U.S. Pat. No. 3,226,421), JP-B-53-18014 (corresponding to U.S. Pat. No. 3,988,359), JP-B-57-26592 (corresponding to U.S. Pat. No. 4,370,279), JP-B-58-2232 (corresponding to U.S. Pat. No 4,228,098), JP-B-61-26419, JP-B-61-58462 (corresponding to U.S. Pat. No. 4,600,541) and JP-B-51-33888 (corresponding to U.S. Pat. No. 4,503,001), (the term "JP-B" as used herein means an "examined Japanese patent publication"), and U.S. Pat. Nos. 4,495,109, 4,192,776, 3,461,150 and 3,338,952.

Some of them have been applied to practical use on an industrial scale, but they sometimes undergo deterioration after long-term use, resulting in reduced yield of the main product, i.e., acrylonitrile. The degree of deterioration widely varies depending on the structure of the reactor used, reaction conditions, and the like.

Various proposals have hitherto been made to regenerate the deteriorated catalysts. For example, catalyst regeneration techniques which can be applied while conducting the reaction include a method of adding a phosphorus component to the reaction system as disclosed in JP-A-53-90238 (corresponding to U.S. Pat. No. 4,124,631) and JP-A-59-139938 (the term "JP-A" as used herein means an "unexamined published Japanese patent application"); a method of adding tellurium and-/or molybdenum as disclosed in JP-A-57-167736 (corresponding to U.S. Pat. No. 4,409,122), JP-A-57-187039 (corresponding to U.S. Pat. Nos. 4,618,593, 4,709,070 and 4,709,071), JP-A-58-139745 (corresponding to U.S. Pat. Nos. 4,618,593, 4,709,070 and 4,709,071), and JP-A-58-140056 (corresponding to European Patent 76,678), U.S. Pat. Nos. 3,168,572 and 4,391,880, and Polish Patent 95,391; a method of adding a molybdenum component as disclosed in JP-A-59-76543 (corresponding to U.S. Pat. No. 4,536,483) and JP-A-59-76544 (corresponding to U.S. Pat. No. 4,757,038); a method of adding an antimony component as disclosed in JP-A-59-90633 (corresponding to U.S. Pat. No. 4,504,599); and a method of adding boron as disclosed in JP-A-59-139940.

Nevertheless, none of these proposals is quite satisfactory from an industrial viewpoint due to disadvantages, such as insufficient effects, insufficient duration of the effects, difficulty in repeated application of the technique, and the like. Hence, industrially applicable techniques for catalyst regeneration have been limited.

In the ammoxidation of propylene for production of acrylonitrile, not only is it important to maintain a high yield of acrylonitrile, but another consideration which is important is by-production of hydrogen cyanide. From an industrial standpoint, a high level of yield of both of these two compounds is required. However, conventional techniques have been developed with the chief object of maintenance of the acrylonitrile yield, and no attention has been directed to maintenance of the hydrogen cyanide yield In other words, difficulty in simultaneously attaining a high level of yield of both acrylonitrile and hydrogen cyanide occurs with conventional techniques.

SUMMARY OF THE INVENTION

Accordingly, one object of this invention is to meet the above-described requirement in the art, providing a process for ammoxidation of propylene in a fluidized bed system, which achieves high yields of not only acrylonitrile, the main product, but also hydrogen cyanide as a useful by-product.

That is, the present invention provides an improved process for long-term ammoxidation of propylene in the presence of a metal oxide catalyst for ammoxidation at a temperature of from 300° C. to 500° C. to produce acrylonitrile and hydrogen cyanide in high yields, wherein each of (A) elemental phosphorus or a phosphorus compound and (B) elemental tellurium or a tellurium compound is added as a regenerating agent at least once to the ammoxidation reaction system as the reaction progresses, the regenerating agent (A) being chosen when the yields of both of acrylonitrile and hydrogen cyanide are reduced, and the regenerating agent (B) being chosen when the yield of acrylonitrile is reduced and the yield of hydrogen cyanide is unchanged or increased.

DETAILED DESCRIPTION OF THE INVENTION

The process of the present invention is applicably equally well to an antimony-containing oxide catalyst as described, for example, in JP-B-38-19111 and U.S. Pat. Nos. 3,152,170, 3,308,151, 3,988,359 and 4,370,279, or a molybdenum-containing oxide catalyst as described, for example, in U.S. Pat. Nos. 2,904,580, 3,226,422, 3,226,421, 4,228,098 and 4,503,011. Implicit in the catalysts to which the process is applicable are:

(i) those represented by formula:

wherein

A represents at least one element selected from the group consisting of Fe, Co, Ni, Mn, Ce, U, Sn, Ti, Cu, and Zn;

B represents at least one element selected from the group consisting of Li, Na, K, Rb, Cs, Be, Mg, Ca, Sr, Ba, Y, La series rare earth elements, Th, Zr, Hf, Nb, Ta, Cr, Re, Ru, Os, Rh, Ir, Pd, Pt, Ag, Au, Cd, Al, Ga, In, Tl, Ge, Pb, As, S, and Se;

C represents at least one element selected from the group consisting of V, Mo, and W;

D represents at least one element selected from the group consisting of B, P, Bi, and Te; and a, b, c, d, e, f, and g each represents the atomic ratio of the respective element and each falls within the following range:

a=2 to 30, preferably 5 to 25;
b=0 to 20, preferably 0 to 15;
c=0 to 10, preferably 0.05 to 10;
d=0 to 10, preferably 0.1 to 10;
e=5 to 50, preferably 10 to 30;
f=a number determined from a, b, c, d, and e necessary to form the respective oxide; and
g=10 to 200, preferably 20 to 150, and (ii) those represented by formula:

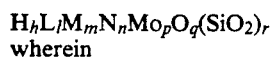

wherein

H represents at least one element selected from the group consisting of Fe, Cr, and Ce;

L represents at least one element selected from the group consisting of Be, Mg, Ca, Sr, Ba, Sc, Y, La series rare earth elements, Th, U, Ti, Zr, Hf, V, Nb, Ta, W, Mn, Re, Co, Ni, Ru, Rh, Pd, Os, Ir, Pt, Cu, Ag, Au, Zn, Cd, Al, Ga, In, Ge, Sn, and Pb;

M represents at least one element selected from the group consisting of Li, Na, K, Rb, Cs, and Tl;

N represents at least one element selected from the group consisting of B, P, As, Sb, Bi, S, Se, and Te;

h, l, m, n, p, q, and r each represents the atomic ratio of the respective element and each falls within the following range:

h=0.5 to 10, preferably 1 to 8;
l=0 to 10, preferably 0 to 8;
m=0 to 5, preferably 0 to 3;
n=0.1 to 10, preferably 0.5 to 8;
p=5 to 15, preferably 6 to 13;
q=a number determined from h, l, m, n, and p necessary to form the respective oxide; and
r=0 to 200, preferably 20 to 150.

While the present invention is characterized by addition of (A) elemental phosphorus or a phosphorus compound (hereinafter referred to as a phosphorus component) and (B) elemental tellurium or a tellurium compound (hereinafter referred to as a tellurium component) to the above-described metal oxide catalyst for ammoxidation, it is not always necessary for the catalyst, the object of regeneration, to contain phosphorus and/or tellurium.

Ammoxidation of propylene may be carried out in either a fixed bed or a fluidized bed, but the effects of the present invention are particularly pronounced when applied to a fluidized bed reaction.

Catalytic activity changes as the reaction proceeds with varying degrees depending on the composition of the catalyst, the structure of the reactor, the reaction conditions, and the like. Industrial problems here are reduction of yield of acrylonitrile and change of yield of the useful by-produced hydrogen cyanide. While reduction in acrylonitrile yield is the most important aspect to consider, the change of hydrogen cyanide yield also poses a serious problem because the over-all process is usually established on the premise that the by-produced hydrogen cyanide can be used for various useful derivatives.

From the viewpoint of practical use, it is preferred that the process according to the present invention is applied when the yield of acrylonitrile or hydrogen cyanide decreases by about 0.5 to 2%. Even if the acrylonitrile or hydrogen cyanide yield is not so much reduced to such extent, it is generally preferred that the acrylonitrile yield and hydrogen cyanide yield is improved by adding the phosphorus component and the tellurium component to maintain a high level of these yields. Where a rapid deterioration of catalyst activity is caused by some abnormal facts such as the deterioration due to reduction, there is a possibility that 2% or more of each yield may be reduced. If this is the case, a rapid application of the present invention is needed, and it is particularly prefferred that the addition of the phosphorus component is preferentially carried out.

In accordance with the present invention, the yields of the acrylonitrile and the hydrogen cyanide increase to the level or more of the fresh catalyst.

In the present invention, a phosphorus component is added to the system when the yields of both acrylonitrile and hydrogen cyanide decrease, and a tellurium component is added when the yield of acrylonitrile is reduced and the yield of hydrogen cyanide remains unchanged or increases. By adding the phosphorus component and the tellurium component while monitoring the change in the reaction characteristics, maintenance of high levels of the acrylonitrile yield and hydrogen cyanide yield can be achieved.

If the phosphorus component is present in excess temporarily or through repeated addition, the reaction undergoes changes such as a reduction in acrylonitrile yield, an increase in hydrogen cyanide yield, and an increase in carbon monoxide yield. If this is the case, the addition of the phosphorus component should be changed to addition of the tellurium component.

On the other hand, when the tellurium component is present in excess temporarily or through repeated addition, the reaction undergoes changes such as a reduction in acrylonitrile yield, and an increase in carbon dioxide yield. On observing these reaction changes, the addition of the tellurium component should be changed to addition of the phosphorus component.

Thus, it is judged by monitoring the changes in the acrylonitrile yield and the hydrogen cyanide yield whether the amount of the phosphorus or tellurium component added is in excess.

The phosphorus component which can be used in the present invention includes elemental phosphorus, phosphorus oxides (e.g., phosphorus trioxide, phosphorus pentoxide), oxyacids of phosphorus (e.g., hypophosphorous acid, phosphorous acid, orthophosphoric acid, condensed phosphoric acid) or salts thereof (e.g., ammonium phosphite, ammonium phosphate, etc.), ammonium polyphosphate, boron phosphate, phosphines, trialkylphosphate, and other inorganic or organic solid phosphorus compounds, either as they are or supported on an inert carrier such as silica, alumina, titania, etc., or a catalyst. Preferred as the phosphorus component are elemental phosphorus and a phosphorus-enriched catalyst comprising a phosphorus compound supported on a catalyst. Addition of the phosphorus component may also be effected by continuously feeding elemental phosphorus, a phosphine, an organic phosphorus compound, etc., in the vapor phase to a reactor for a prescribed period of time.

The tellurium component which can be used in the present invention includes elemental tellurium, tellurium dioxide, tellurium trioxide, tellurous acid, telluric acid, tellurium methoxide, tellurium ethoxide, and other organic or inorganic solid tellurium compounds, either as they are or supported on an inert carrier such as silica, alumina, titania, etc., or a catalyst. Preferred as a tellurium component are elemental tellurium and a tellurium-enriched catalyst comprising a tellurium compound supported on a catalyst. Addition of the tellurium component may also be effected by continuously feeding elemental tellurium, hydrogen telluride, an organic tellurium compound, etc., in the vapor phase to a reactor for a prescribed period of time.

The amount of the phosphorus component to be added each time is in the range of from 0.01 to 10, preferably from 0.05 to 5, expressed as an atomic ratio, per 100 of antimony in an antimony-containing oxide catalyst or per 100 of molybdenum in a molybdenum-containing oxide catalyst.

The amount of the tellurium component to be added each time is in the range of from 0.05 to 10, preferably from 0.1 to 5, expressed as an atomic ratio, per 100 of antimony in an antimony-containing oxide catalyst or per 100 of molybdenum in a molybdenum-containing oxide catalyst.

The addition of the phosphorus component and tellurium component can be effected repeatedly while monitoring the reaction characteristics. The added phosphorus component and tellurium component tend to be lost due to gradual escape from the reaction system, though the degree of the loss varies depending on the reaction conditions. The phosphorus component shows this tendency more conspicuously than the tellurium component. Where such a tendency is observed causing changes in the reaction results, due consideration should be given to the situation and, accordingly, the necessary component should be added repeatedly.

Conventional conditions for ammoxidation of propylene can be used as described, for example, in U.S. Pat. Nos. 4,124,631, 4,409,122, 4,618,593, 4,709,070, 4,709,071, 3,168,572, 4,391,880, 4,536,483, 4,757,038 and 4,504,599. In greater detail, propylene, oxygen and ammonia are fed in a gaseous phase at a molar ratio of 1:0.3–10:0.5–5. If desired, the gaseous mixture may contain nitrogen, steam, carbon dioxide, helium, etc., as a diluting gas. The reaction temperature is in the range of from 300° to 500° C., and the apparent contact time is from 0.1 to 20 seconds.

According to the process of this invention, the phosphorus component and tellurium component added exert their effects by deposition on the catalyst during the ammoxidation reaction. Although a detailed operative mechanism of these components has not yet been elucidated, it is believed that the active centers of the catalyst are effectively modified through deposition of the phosphorus component and tellurium component.

Addition of the phosphorus component is effective to increase the yield of hydrogen cyanide, while that of the tellurium component is accompanied by reduction in the hydrogen cyanide yield. When only the phosphorus component is added in excess or added repeatedly, resulting in an increase of production of carbon monoxide and hydrogen cyanide, it is difficult to improve the yield of acrylonitrile. On the other hand, addition of only the tellurium component leads to a reduction in the yield of hydrogen cyanide, and improvement of such a situation would be sometimes difficult.

Therefore, an appropriate combination of the addition of the phosphorus component and the addition of the tellurium component, taking advantage of the characteristics of each component, can first make it possible to maintain both the yield of acrylonitrile and the yield of hydrogen cyanide at high levels without involving the above-described disorders which would happen on addition of only one of them.

Another advantage of this invention arising as a result of the combined addition of the phosphorus component and the tellurium component is that a reduction in the rate of loss and prolonged duration of the component is achieved as compared with an addition of either one of them alone.

The present invention is now illustrated in greater detail by way of the following Examples and Comparative Examples, but it should be understood that the present invention is not deemed to be limited thereto. Unless otherwise indicated herein, all parts, percents, ratios and the like are by weight.

In these examples, yields of products were calculated from the following equation:

$$\text{Yield}(\%) = \frac{\text{Weight (g) of Carbon in Product}}{\text{Weight (g) of Carbon in Propylene Charged}} \times 100$$

The experimental ammoxidation reaction of propylene for testing catalytic activity was conducted as follows. A catalyst being tested was charged in a fluidized bed reactor, the catalyst moving portion of which had an inner diameter of 2 inch. A mixed gas consisting of air, propylene, and ammonia at an air/propylene molar ratio of 10.2:1 and at an ammonia/propylene molar ratio of 1.05:1 was fed to the reactor at an apparent linear velocity of 8 cm/sec. The reaction pressure was set at 0.8 kg/cm$^2$G.

EXAMPLE 1

Application of Invention to Fairly Deteriorated Catalyst:

A propylene ammoxidation system which had been carried on for a considerable period of time by using a catalyst of the formula:

$Fe_{12}Cu_3Sb_{25}W_{0.5}Te_{1.25}O_{75}(SiO_2)_{60}$ failed to maintain a prescribed feed rate of air due to disorder of a compressor and, therefore, the reaction was stopped.

After the reaction was stopped, the catalyst was withdrawn and subjected to activity testing under the above-described conditions. It was determined that both the yield of acrylonitrile and the yield of hydrogen cyanide were greatly reduced, with increased production of carbon dioxide, proving the catalyst was deteriorated.

Red phosphorus was added to the testing system. Upon continuing the reaction, the yield of acrylonitrile and the yield of hydrogen cyanide were both improved, while the production rate of carbon dioxide decreased from 14.2% to 8.5%. At the point when the reaction was continued for 25 hours from the addition of the phosphorus component, metallic tellurium was added to the reaction system. As a result, the yield of acrylonitrile showed a further improvement, with the yield of hydrogen cyanide remaining almost unchanged. The results of the series of tests are shown in Table 1.

TABLE 1

| Catalyst Under Test | Amount of P or Te Added (Atomic Ratio) Per Sb = 100 | Time Elapsed from Addition of P or Te/Total Reaction Time (hr/hr) | Yield | | |
|---|---|---|---|---|---|
| | | | $C_3H_3N$ (%) | HCN (%) | $C_3H_3N$ + HCN (%) |
| Fresh | — | — | 80.1 | 5.2 | 85.3 |
| Deteriorated | — | —/1.5 | 75.9 | 3.3 | 79.2 |
| After Addition of P Component | 0.8 | 1.5/4.7 | 78.3 | 4.8 | 83.1 |
| After Addition of Te Component | 0.4 | 1.5/29.7 | 79.4 | 4.7 | 84.1 |

COMPARATIVE EXAMPLE 1

Metallic tellurium was added to the same experimental reaction system as used in Example 1 charged with deteriorated catalyst, and the reaction was further carried on. The results of the reaction are shown in Table 2. It can be seen that the yield of acrylonitrile was improved, but the production of carbon dioxide was still high, and no substantial improvement in the hydrogen cyanide yield took place.

TABLE 2

| Catalyst Under Test | Amount of Te Added (Atomic Ratio) Per Sb = 100 | Time elapsed from Addition of Te/Total Reaction Time (hr/hr) | Yield | | |
|---|---|---|---|---|---|
| | | | $C_3H_3N$ (%) | HCN (%) | $C_3H_3N$ + HCN (%) |
| Fresh | — | — | 80.1 | 5.2 | 85.3 |
| Deteriorated | — | —/1.5 | 75.9 | 3.3 | 79.2 |
| After Addition of Te Component | 0.4 | 1.5/5.0 | 77.2 | 3.1 | 80.3 |

COMPARATIVE EXAMPLE 2

Red phosphorus was added to the same experimental reaction system as used in Example 1 charged with the deteriorated catalyst, and the reaction was further carried out. It was confirmed that the production of carbon dioxide was reduced and both the yield of acrylonitrile and the yield of hydrogen cyanide were improved. Thereafter, the reaction was further continued. Since the degree of improvements in the yields of acrylonitrile and hydrogen cyanide were still unsatisfactory, red phosphorus was again added to the reaction system. As a result, the yield of hydrogen cyanide was slightly improved, whereas no substantial improvement in the yield of acrylonitrile was observed and the production of carbon monoxide increased. The results of the series of the tests are shown in Table 3.

TABLE 3

| Catalyst Under Test | Amount of Te Added (Atomic Ratio) Per Sb = 100 | Time Elapsed from Addition of P/Total Reaction Time (hr/hr) | Yield | | |
|---|---|---|---|---|---|
| | | | $C_3H_3N$ (%) | HCN (%) | $C_3H_3N$ + HCN (%) |
| Fresh | — | — | 80.1 | 5.2 | 85.3 |
| Deteriorated | — | —/1.5 | 75.9 | 3.3 | 79.2 |
| After First Addition of P | 0.8 | 1.5/5.0 | 78.2 | 4.9 | 83.1 |
| After Second Addition of P | 0.8 | 1.5/23.5 | 78.6 | 5.3 | 83.9 |

EXAMPLE 2

Long-Term Maintenance of Catalytic Performance

When a catalyst of the formula:

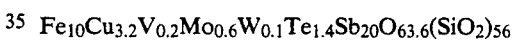
$$Fe_{10}Cu_{3.2}V_{0.2}Mo_{0.6}W_{0.1}Te_{1.4}Sb_{20}O_{63.6}(SiO_2)_{56}$$

was used for a long period of time in ammoxidation of propylene in a pilot apparatus, both the yield of acrylonitrile and the yield of hydrogen cyanide were reduced.

The catalyst was withdrawn and subjected to activity testing under the above-described conditions as follows. With the progress of the experimental reaction, a metallic tellurium powder as a tellurium component and an ammonium phosphate powder as a phosphorus component were separately and repeatedly added to the reaction system according to the schedule indicated in Table 4 below. The changes in the reaction results are shown in Table 4 below also.

TABLE 4

| Catalyst Under Test | Amount of Te or P Added (Atomic Ratio) Per Sb = 100 | Time Elapsed from Addition of Te or P/Total Reaction Time (hr/hr) | Yield | | |
|---|---|---|---|---|---|
| | | | $C_3H_3N$ (%) | HCN (%) | $C_3H_3N$ + HCN (%) |
| Fresh | — | — | 75.3 | 5.2 | 80.5 |
| Deteriorated | — | —/2.1 | 74.4 | 5.0 | 79.4 |

TABLE 4-continued

| Catalyst Under Test | Amount of Te or P Added (Atomic Ratio) Per Sb = 100 | Time Elapsed from Addition of Te or P/Total Reaction Time (hr/hr) | Yield C$_3$H$_3$N (%) | HCN (%) | C$_3$H$_3$N + HCN (%) |
|---|---|---|---|---|---|
| (i) After First Addition of Te | 0.6 | 3.4/5.5 | 75.3 | 4.3 | 79.6 |
| (ii) After First Addition of P | 1.2 | 2.5/8.0 | 75.5 | 5.3 | 80.8 |
|  |  | 20/25.5 | 75.2 | 5.3 | 80.5 |
|  |  | 105/110.5 | 75.0 | 5.1 | 80.1 |
|  |  | 170/175.5 | 75.2 | 5.3 | 80.5 |
| (iii) After Second Addition of P | 0.8 | 14.2/189.7 | 75.3 | 5.5 | 80.8 |
| (iv) After Third Addition of P | 0.8 | 23/212.7 | 75.0 | 5.4 | 80.4 |
| (v) After Second Addition of Te | 0.6 | 18.4/232.0 | 75.5 | 5.1 | 80.6 |

EXAMPLE 3

When a catalyst of the formula:

$$Fe_{9.9}Cu_{2.4}Zn_{0.3}Mo_{0.3}W_{0.1}P_{0.1}B_{0.3}Te_{0.8}Sb_{15}O_{46.1}(SiO_2)_{36}$$

was used for a long period of time in ammoxidation of propylene in a pilot apparatus, both the yield of acrylonitrile and the yield of hydrogen cyanide were reduced.

The catalyst was withdrawn and subjected to activity testing under the above-described conditions as follows. With the progress of the experimental reaction, a tellurium component and a phosphorus component were added to the reaction system in the order to Te component—P component—Te component according to the schedule indicated in Table 5 below. The changes in reaction results are shown in Table 5 below also.

The P component used in this example was a phosphorus-enriched catalyst prepared by impregnating phosphoric acid into the catalyst used here, drying, and calcining. The Te component used in this example was a tellurium-enriched catalyst prepared by impregnating the catalyst used here with aqueous hydrogen peroxide having dissolved therein metallic tellurium with the aid of ammonium paramolybdate, drying, and calcining.

TABLE 5

| Catalyst Under Test | Amount of Te or P Added (Atomic Ratio) Per Sb = 100 | Time Elapsed from Addition of Te or P/Total Reaction Time (hr/hr) | Yield C$_3$H$_3$N (%) | HCN (%) | C$_3$H$_3$N + HCN (%) |
|---|---|---|---|---|---|
| Fresh | — | — | 76.6 | 5.2 | 81.8 |
| Deteriorated | — | —/1.8 | 75.5 | 5.3 | 81.0 |
| (i) After First Addition of Te | 0.6 | 5.2/7.0 | 76.5 | 5.1 | 81.6 |
|  |  | 120/127 | 76.3 | 5.2 | 81.5 |
| (ii) After First Addition of P | 0.5 | 21.3/145.3 | 76.7 | 5.3 | 81.9 |
|  |  | 56/180 | 76.5 | 5.4 | 81.9 |
| (iii) After Second Addition of Te | 0.3 | 5.5/201.5 | 76.9 | 5.2 | 82.1 |

EXAMPLE 4

When a catalyst of the formula:

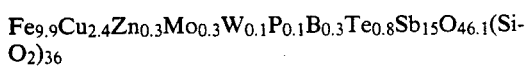

was used for a long period of time in ammoxidation of propylene in a pilot apparatus, both the yield of acrylonitrile and the yield of hydrogen cyanide were reduced.

The catalyst was withdrawn and subjected to activity testing under the above-described conditions as follows. With the progress of the experimental reaction, an ammonium phosphate powder as a P component and a metallic tellurium powder as a Te component were added to the reaction system in the order of Te component—P component in accordance with the schedule indicated in Table 6 below. The changes of reaction results are shown in Table 6 below also.

TABLE 6

| Catalyst Under Test | Amount of Te or P Added (Atomic Ratio) Per Mo = 100 | Time Elapsed from Addition of Te or P/Total Reaction Time (hr/hr) | Yield C$_3$H$_3$N (%) | HCN (%) | C$_3$H$_3$N + HCN (%) |
|---|---|---|---|---|---|
| Fresh | — | — | 71.5 | 8.2 | 79.7 |
| Deteriorated | — | —/2.0 | 70.2 | 9.0 | 79.2 |
| (i) After Te Addition | 0.6 | 3.5/5.3 | 73.6 | 7.5 | 81.1 |
|  |  | 78/80 | 73.4 | 7.7 | 81.1 |
| (ii) After P Addition | 0.4 | 8.3/91.8 | 73.8 | 8.0 | 81.8 |
|  |  | 54/137.5 | 73.5 | 8.2 | 81.7 |

While the invention has been described in detail and with reference to specific embodiments thereof, it will be apparent to one skilled in the art that various changes and modifications can be made therein without departing from the spirit and scope thereof.

What is claimed is:

1. A process for conducting long-term ammoxidation of propylene in the presence of a metal oxide catalyst for ammoxidation of propylene at a temperature of from 300° C. to 500° C. to produce acrylonitrile and hydrogen cyanide where yields of acrylonitrile and hydrogen cyanide are maintained at the level of or more than that obtained with the fresh metal oxide catalyst, wherein each of
   (A) elemental phosphorus or a phosphorus compound and
   (B) elemental tellurium or a tellurium compound is added as a catalyst regenerating agent at least once to the ammoxidation reaction system as the reaction progresses, said regenerating agent (A) is added when the yields of both of acrylonitrile and hydrogen cyanide are reduced as compared to the yields obtained with the fresh metal oxide catalyst, and the regenerating agent (B) is added when the yield of acrylonitrile is reduced and the yield of hydrogen cyanide is unchanged or increased compared to the yield obtained with the fresh metal oxide catalyst.

2. A process as claimed in claim 1, wherein said metal oxide catalyst for ammoxidation is selected from the group consisting of (i) an antimony-containing oxide catalyst represented by formula:

$$A_a B_b C_c D_d Sb_e O_f (SiO_2)_g$$

wherein
   A represents at least one element selected from the group consisting of Fe, Co, Ni, Mn, Ce, U, Sn, Ti, Cu, and Zn;
   B represents at least one element selected from the group consisting of Li, Na, K, Rb, Cs, Be, Mg, Ca, Sr, Ba, Y, La series rare earth elements, Th, Zr, Hf, Nb, Ta, Cr, Re, Ru, Os, Rh, Ir, Pd, Pt, Ag, Au, Cd, Al, Ga, In, Tl, Ge, Pb, As, S, and Se;
   C represents at least one element selected from the group consisting of V, Mo, and W;
   D represents at least one element selected from the group consisting of B, P, Bi, and Te; and
   a, b, c, d, e, f, and g each represents the atomic ratio of the respective element and each falls within the following range:
   a=2 to 30;
   b=0 to 20;
   c=0 to 10;
   d=0 to 10;
   e=5 to 50;
   f=a number determined from a, b, c, d, and e necessary to form the respective oxides; and
   g=10 to 200,
and (ii) a molybdenum-containing oxide catalyst represented by the formula:

$$H_h L_l M_m N_n Mo_p O_q (SiO_2)_r$$

wherein
   H represents at least one element selected from the group consisting of Fe, Cr, and Ce;
   L represents at least one element selected from the group consisting of Be, Mg, Ca, Sr, Ba, Sc, Y, La series rare earth elements, Th, U, Ti, Zr, Hf, V, Nb, Ta, W, Mn, Re, Co, Ni, Ru, Rh, Pd, Os, Ir, Pt, Cu, Ag, Au, Zn, Cd, Al, Ga, In, Ge, Sn, and Pb;
   M represents at least one element selected from the group consisting of Li, Na, K, Rb, Cs, and Tl;
   N represents at least one element selected from the group consisting of B, P, As, Sb, Bi, S, Se, and Te;
   h, l, m, n, p, q, and r each represents the atomic ratio of the respective element and each falls within the following range:
   h=0.5 to 10;
   l=0 to 10;
   m=0 to 5;
   n=0.1 to 10;
   p=5 to 15;
   q=a number determined from h, l, m, n, and p necessary to form the respective oxides; and
   r=0 to 200.

3. A process as claimed in claim 1, wherein said phosphorus compound is selected from the group consisting of phosphorus trioxide, phosphorus pentoxide, hypophosphorous acid, phosphorous acid, orthophosphoric acid, condensed phosphoric acid, ammonium phosphite, ammonium phosphate, ammonium polyphosphate, boron phosphate, phosphines, and trialkylphosphate.

4. A process as claimed in claim 1, wherein said elemental phosphorus or phosphorus compound is supported on an inert carrier or a catalyst.

5. A process as claimed in claim 1, wherein the regenerating agent (A) is elemental phosphorus or a phosphorus-enriched catalyst comprising a phosphorus compound supported on a metal oxide catalyst for ammoxidation.

6. A process as claimed in claim 1, wherein said tellurium compound is selected from the group consisting of tellurium dioxide, tellurium trioxide, tellurous acid, telluric acid, tellurium methoxide and tellurium ethoxide.

7. A process as claimed in claim 1, wherein said elemental tellurium or tellurium compound is supported on an inert carrier or a catalyst.

8. A process as claimed in claim 1, wherein the regenerating agent (B) is elemental tellurium or a tellurium-enriched catalyst comprising a tellurium compound supported on a metal oxide catalyst for ammoxidation.

9. A process as claimed in claim 1, wherein the regenerating agent (A) added each time in an amount ranging from 0.01 to 10, expressed as an atomic ratio, per 100 of antimony in an antimony-containing oxide catalyst or per 100 of molybdenum in a molybdenum-containing oxide catalyst and the regenerating agent (B) is added each time in an amount ranging from 0.05 to 10, expressed as an atomic ratio, per 100 g antimony in an antimony-containing oxide catalyst or per 100 of molybdenum in a molybdenum-containing oxide catalyst.

* * * * *